United States Patent
Thomas et al.

(10) Patent No.: US 7,997,122 B2
(45) Date of Patent: Aug. 16, 2011

(54) REID VAPOR PRESSURE ANALYZER WITH AN AIR SATURATOR

(75) Inventors: Thomas J. Thomas, Lewisburg, WV (US); Terry E. Davis, Rainelle, WV (US)

(73) Assignee: ABB Inc., Cary, NC (US)

( * ) Notice: Subject to any disclaimer, the term of this patent is extended or adjusted under 35 U.S.C. 154(b) by 514 days.

(21) Appl. No.: 12/184,620

(22) Filed: Aug. 1, 2008

(65) Prior Publication Data

US 2009/0188306 A1 Jul. 30, 2009

Related U.S. Application Data

(60) Provisional application No. 60/956,035, filed on Aug. 15, 2007.

(51) Int. Cl.
*G01N 7/00* (2006.01)
(52) U.S. Cl. ....................................... 73/64.45
(58) Field of Classification Search .............. 73/64.45
See application file for complete search history.

(56) References Cited

U.S. PATENT DOCUMENTS

| | | | |
|---|---|---|---|
| 3,499,317 A | * | 3/1970 | Hook ............... 73/64.45 |
| 4,332,159 A | | 6/1982 | Chin et al. |
| 4,522,056 A | | 6/1985 | Chin et al. |
| 5,022,259 A | | 6/1991 | Lee et al. |
| 5,563,339 A | | 10/1996 | Compton et al. |
| 6,422,465 B2 | | 7/2002 | Miller |

FOREIGN PATENT DOCUMENTS

GB 2329218 A * 3/1999

* cited by examiner

*Primary Examiner* — Hezron E Williams
*Assistant Examiner* — Alex Devito
(74) *Attorney, Agent, or Firm* — Paul R. Katterle

(57) ABSTRACT

The present invention is directed to an analyzer for measuring the vapor pressure of a hydrocarbon liquid. The analyzer includes a pressure measuring system connected to an air saturation system having a circulation chamber with opposing first and second ends. A first opening is disposed toward the first end and a second opening is disposed toward the second end. A plumbing system connects the first and second openings. A pump moves the hydrocarbon liquid through the plumbing system from the first opening to the second opening so as to saturate the hydrocarbon liquid with air. The air saturation system has a cooler for cooling the hydrocarbon liquid and the pressure measuring system has a heater for heating the hydrocarbon liquid. The pump may be a piston actuated pump or a motor-driven pump and the plumbing system may include an aeration chamber.

20 Claims, 12 Drawing Sheets

US 7,997,122 B2

REID VAPOR PRESSURE ANALYZER WITH AN AIR SATURATOR

CROSS-REFERENCE TO RELATED APPLICATION

This application claims the benefit of U.S. provisional patent application No. 60/956,035 filed on Aug. 15, 2007, which is hereby incorporated by reference in its entirety.

BACKGROUND OF THE INVENTION

The present invention is directed toward analyzers for measuring vapor pressure and more particularly toward an air saturator for an analyzer that measures the Reid vapor pressure of volatile liquids.

The vapor pressure of a liquid or solid is the pressure exerted when the liquid or solid is in equilibrium with its own vapor. As such, vapor pressure is a measure of the tendency of a substance to vaporize and, thus, provides an indication of the volatility of the substance. The volatility of liquid fuel, such as gasoline, is important for both environmental and performance reasons. Fuel vapor is a major contributor to air pollution, which has prompted the Environmental Protection Agency (EPA) to enact regulations to limit evaporative fuel losses. In addition, if a fuel is too volatile and vaporizes too quickly, fuel flow within a vehicle may be adversely impacted so as to cause rough engine operation or stoppage. On the other hand, if fuel for a vehicle is not sufficiently volatile, the fuel may cause hard starting and poor warm-up of the vehicle, as well as unequal fuel distribution among the engine cylinders of the vehicle. For the foregoing reasons, it is important for fuel refiners to produce fuel with a volatility that provides optimal vehicle performance and meets environmental regulations. In order to do so, fuel refiners must be able to accurately measure the vapor pressure, more specifically, the Reid vapor pressure of the fuel they are producing. The Reid vapor pressure is the equilibrium pressure at 37.8° C. (100° F.) of a liquid having an initial boiling point above 0° C. (32° F.).

Since the Reid vapor pressure of a liquid mixture with differing component vapor pressures depends on a number of factors, such as the temperature, the ratio of vapor space to liquid volume in the liquid's container and the amount of dissolved air in the liquid mixture, standard test methods for measuring Reid vapor pressure have been established to reduce measurement variations due to these factors. One such standard test method has been established by the American Society for Testing Materials and is designated as ASTM D-323. In order to reduce variations in Reid vapor pressure measurement due to variations in air saturation, ASTM D-323 requires uniform saturation of a test sample with dissolved air at a temperature between 32° F. and 40° F. Since ASTM D-323 is adapted for use in a laboratory, ASTM D-323 specifies that the air saturation of a test sample is performed by manually shaking a container containing the test sample.

For most fuel refiners it is impractical to continuously perform manual tests on fuel samples in a laboratory. Therefore, fuel refiners typically measure Reid vapor pressure on a continual basis using Reid vapor pressure (RVP) analyzers. Conventional RVP analyzers do not saturate a test sample with air in accordance with ASTM D-3232. Instead, conventional RVP analyzers make corrections to compensate for the partial pressure of dissolved air which may be present in the samples tested. These corrections are not always accurate and may lead to inaccurate results.

Based on the foregoing, there is a need for an RVP analyzer having an air saturator that saturates test samples with air at a temperature between 32° F. and 40° F. The present invention is directed to such an RVP analyzer with an air saturator.

SUMMARY OF THE INVENTION

In accordance with the present invention, an analyzer for measuring the vapor pressure of a hydrocarbon liquid is provided. The analyzer includes a pressure measuring system and an air saturation system. The pressure measuring system includes a measuring cell for holding the hydrocarbon liquid and a pressure sensor for measuring the pressure within the measuring cell. The air saturation system is connected to the pressure measuring system and is operable to provide the hydrocarbon liquid to the measuring cell. The air saturation system has first and second chambers and a pump operable to move the hydrocarbon liquid back and forth between the first and second chambers so as to saturate the hydrocarbon liquid with air.

Also provided in accordance with the present invention is an analyzer for measuring the vapor pressure of a hydrocarbon liquid. The analyzer includes a pressure measuring system and an air saturation system. The pressure measuring system includes a measuring cell for holding the hydrocarbon liquid and a pressure sensor for measuring the pressure within the measuring cell. The air saturation system is connected to the pressure measuring system and is operable to provide the hydrocarbon liquid to the measuring cell. The air saturation system includes a circulation chamber with opposing first and second ends. The circulation chamber has a first opening disposed toward the first end and a second opening disposed toward the second end. A plumbing system connects the first and second openings together. A pump is operable to move hydrocarbon liquid through the plumbing system from the first opening to the second opening so as to saturate the hydrocarbon liquid with air.

BRIEF DESCRIPTION OF THE DRAWINGS

The features, aspects, and advantages of the present invention will become better understood with regard to the following description, appended claims, and accompanying drawings where:

DETAILED DESCRIPTION OF ILLUSTRATIVE EMBODIMENTS

Figure 1:
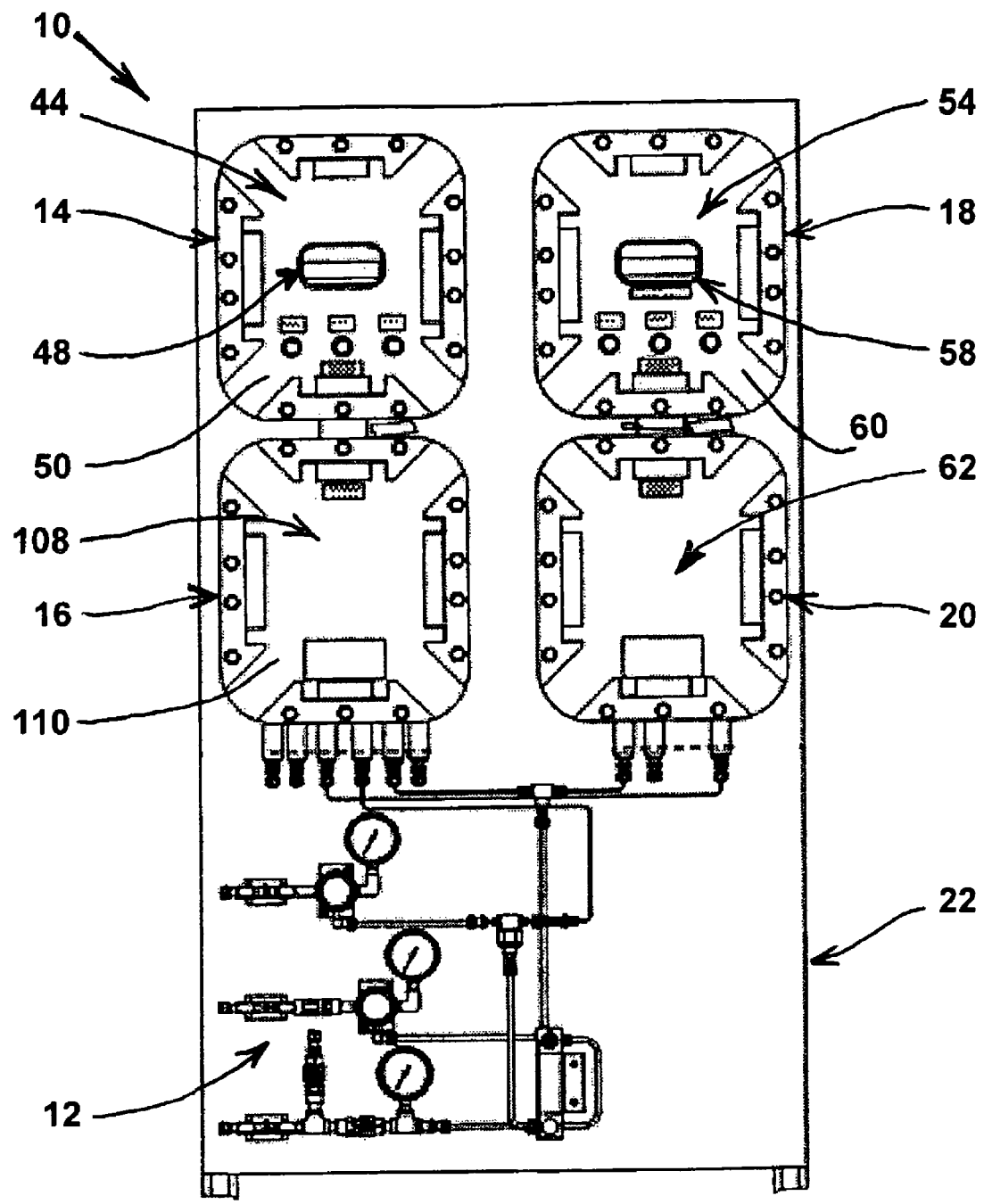
FIG. 1 is a front elevational view of a vapor pressure analyzer embodied in accordance with the present invention.

It should be noted that in the detailed description that follows, identical components have the same reference numerals, regardless of whether they are shown in different embodiments of the present invention. It should also be noted that in order to clearly and concisely disclose the present invention, the drawings may not necessarily be to scale and certain features of the invention may be shown in somewhat schematic form.

Referring now to FIG. 1 there is shown a Reid vapor pressure (RVP) analyzer 10 embodied in accordance with the present invention. Generally, the RVP analyzer 10 comprises a sample system 12, an air saturation electronics assembly 14, an air saturation process assembly 16, an RVP electronics assembly 18 and an RVP process assembly 20. The RVP analyzer 10 may be mounted on a wall, a rack, or a floor stand 22 (as shown).

Figure 2:
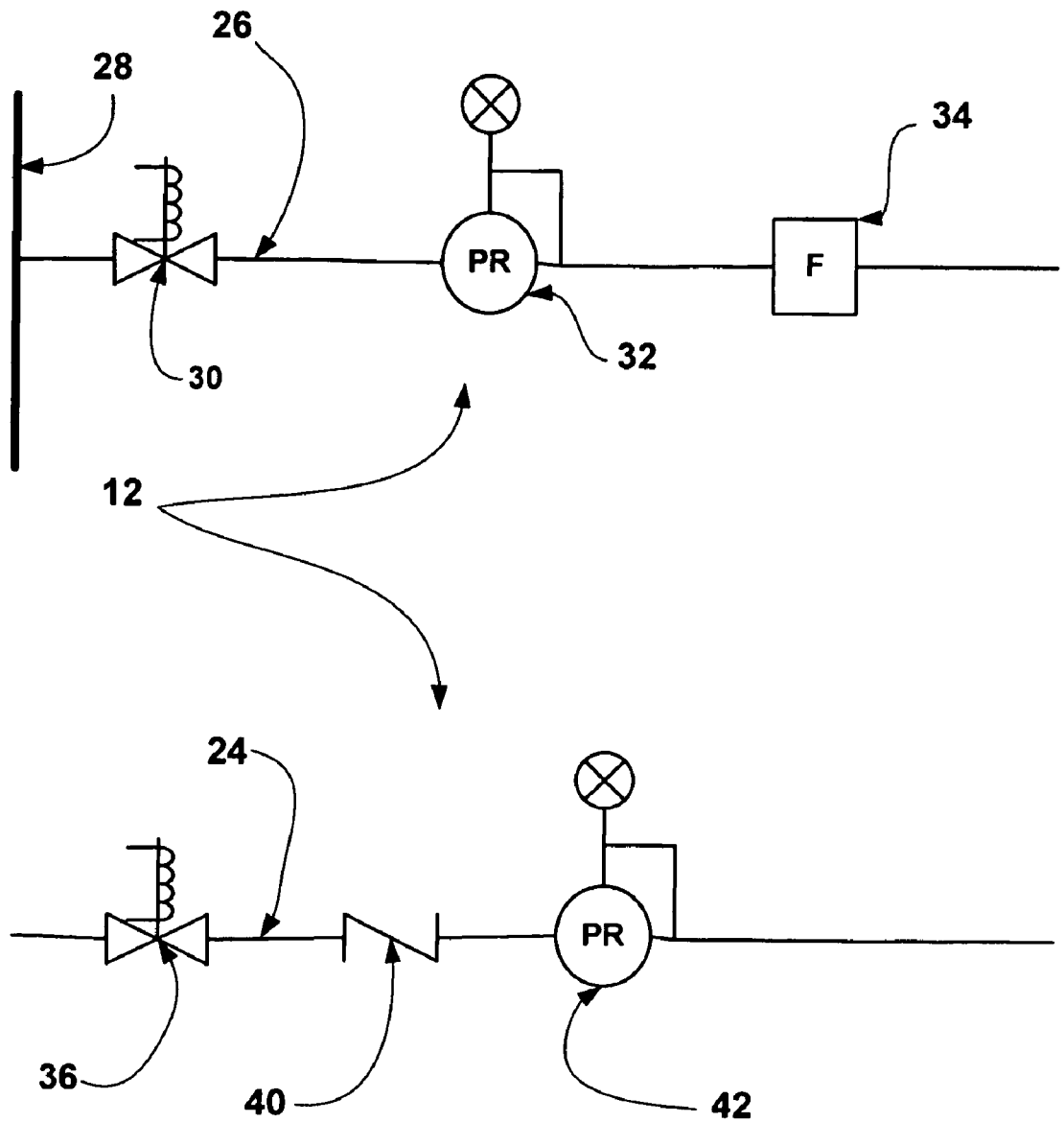
FIG. 2 is a schematic view of a sample system of the vapor pressure analyzer.

Referring now to FIG. 2, the sample system 12 includes an air inlet line 24 for connection to a source of pressurized air and a sample input line 26 for connection to a process line 28 carrying a hydrocarbon liquid that is to have its Reid vapor pressure measured. A solenoid-actuated sample shut-off valve 30, a pressure regulator 32 with an indicator and a bypass filter 34 are connected into the sample input line 26. A solenoid-actuated air shut-off valve 36, a check valve 40 and a pressure regulator 42 with an indicator are connected into the air inlet line 24. The process line 28 provides the hydrocarbon liquid (sample liquid) to the sample input line 26 at a pressure of about 60 psig, while the source of pressurized air provides air to the air inlet line 24 also at a pressure of about 60 psig. The pressure regulator 32 reduces the pressure of the sample liquid to about 40 psig, and the pressure regulator 42 also reduces the pressure of the air to about 40 psig. The sample input line 26 is connected to the air saturation process assembly 16, while the air inlet line 24 is connected to both the RVP process assembly 20 and the air saturation process assembly 16.

Referring back to FIG. 1, the air saturation electronics assembly 14 has an explosion-proof housing 44 that encloses a cooler power supply (not shown) and one or more circuit boards (not shown) containing one or more air saturation (AS) microprocessors 46 (shown in FIG. 4) with associated memory 47 for controlling the operation of the air saturation process assembly 16. An operator interface 48 is mounted on a door 50 of the housing 44 and includes an LCD display and pushbutton switches. The circuit boards and the AS microprocessor(s) 46 mounted thereon are connected by wiring to the air saturation process assembly 16 for communication therewith.

The RVP electronics assembly 18 has an explosion-proof housing 54 that encloses one or more circuit boards (not shown) containing memory and one or more RVP microprocessors 56 (shown in FIG. 3) for controlling the operation of the RVP process assembly 20. An operator interface 58 is mounted on a door 60 of the housing 54 and includes an LCD display and pushbutton switches. The circuit boards and the RVP microprocessor(s) 56 mounted thereon are connected by wiring to the RVP process assembly 20 for communication therewith.

Figure 3:
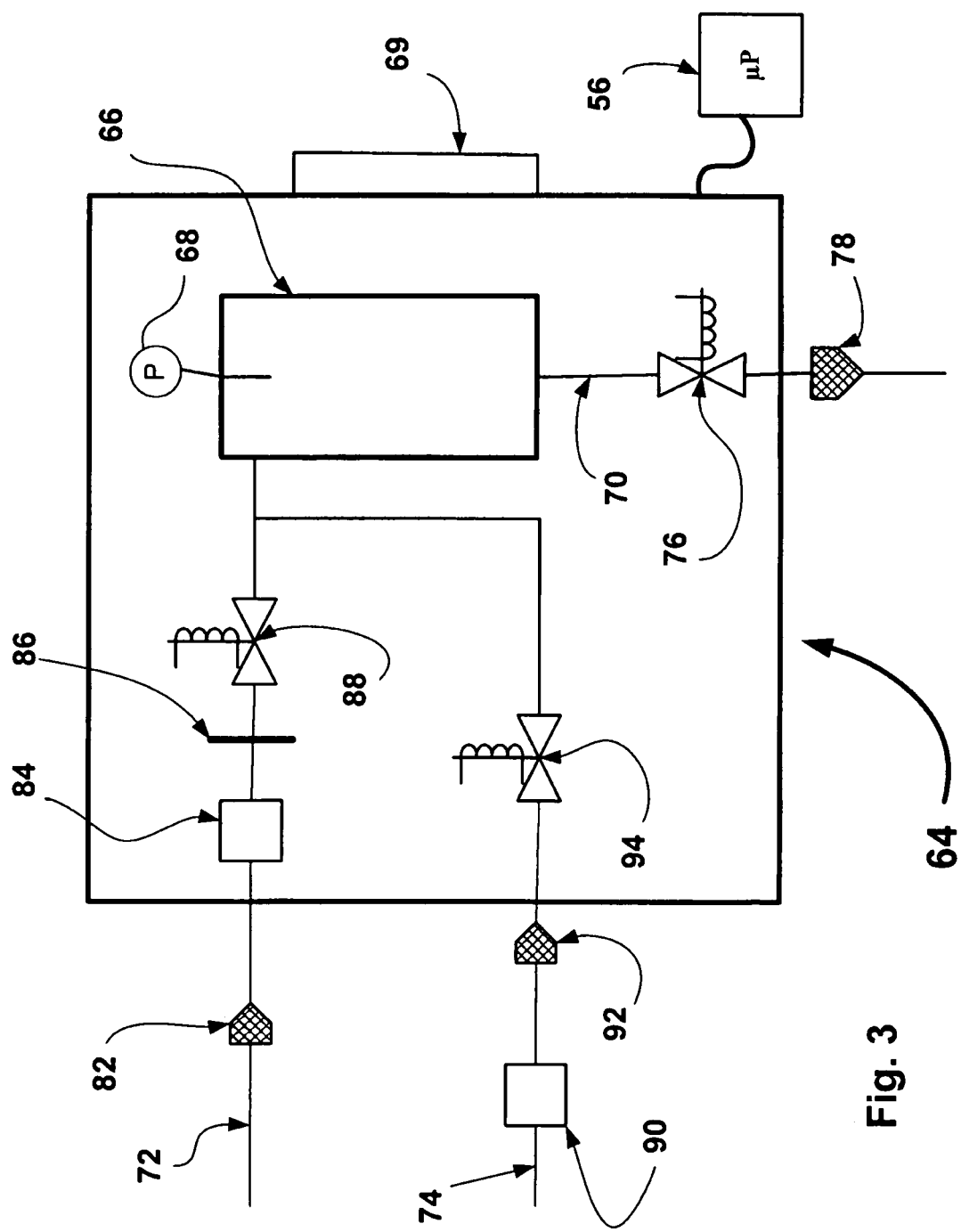
FIG. 3 is a schematic view of a Reid vapor pressure unit of the vapor pressure analyzer.

The RVP process assembly 20 has an explosion-proof housing 62 that encloses an RVP unit 64 with a measuring cell 66, which are shown in FIG. 3. A pressure sensor 68 is provided for measuring the pressure inside the measuring cell 66 and a level sensor (not shown) is provided for determining when the level of sample liquid inside the measuring cell 66 reaches a predetermined fill level. An electrical resistance heater 69 is also provided and is operable to heat the RVP unit 64. A drain line 70, a sample input line 72 and an air purge line 74 are connected to the measuring cell 66. The air purge line 74 is connected to the air inlet line 24 of the sample system 12, while the sample input line 72 is connected to the air saturation process assembly 16. A solenoid-actuated drain valve 76 and a flameproof breather 78 are connected into the drain line 70. A flameproof breather 82, a filter 84, an orifice 86 and a solenoid-actuated sample valve 88 are connected into the sample input line 72. A screened orifice 90, a flameproof breather 92 and a solenoid-actuated purge valve 94 are connected into the air purge line 74. The air purge line 74 is connected to the sample input line 72, which, in turn, is connected to an opening in a top portion of the measuring cell 66. The drain valve 76, the sample valve 88 and the purge valve 94 are connected to the RVP microprocessor 56. A software routine stored in memory is executed by the RVP microprocessor 56 to perform an analysis process in the RVP measuring cell 66.

The analysis process begins with the heater being energized to heat the measuring cell 66 to a temperature of 100° F. When the measuring cell 66 reaches 100° F., a diagnostic test is performed to ensure that the level sensor is operating properly. After a successful diagnostic test, the purge valve 94 and the drain valve 76 open for a brief period of time, such as 20 seconds, so that pressurized air from the air purge line 74 purges the measuring cell 66 and the drain line 70. The RVP microprocessor 56 also sends a fill request signal to the AS microprocessor 46 to provide sample liquid from the air saturation process assembly 16. The purge valve 94 and the drain valve 76 then close. The sample valve 88 is then opened so that 2.5 ml of sample liquid from the air saturation process assembly 16 moves through the sample input line 72 and into the measuring cell 66. When the sample liquid reaches the fill level, as determined by the level sensor, the sample valve 88 closes and the drain valve 76 opens to empty the measuring cell 66. This "false fill" rinses the measuring cell 66 and associated plumbing with new sample liquid, thereby removing any residue from the previous sample. After the false fill, the drain valve 76 remains open and the purge valve 94 opens for another brief period of time, such as 20 seconds, so that pressurized air from the air purge line 74 purges the measuring cell 66 and the drain line 70. The foregoing false fill and subsequent air purge is repeated another two times, for a total of three false fills and four air purges.

After the last air purge, the drain valve 76 remains open and the temperature of the measuring cell 66 is allowed to reach 100° F. again. In this regard, it should be noted that the false fills and the air purges tend to cause the temperature of the measuring cell 66 to drop below 100° F. When the measuring cell 66 reaches 100° F., the pressure in the measuring cell 66, as measured by the pressure sensor 68, is recorded and stored as a zero pressure measurement. The drain valve 76 is then closed and the sample valve 88 is opened so that 2.5 ml of sample liquid from the air saturation process assembly 16 moves through the sample input line 72 and into the measuring cell 66. As the sample liquid fills the measuring cell 66, the heater heats the measuring cell 66 to counteract the cooling effect of the cooled sample liquid and thereby maintain the temperature of the measuring cell 66 at 100° F. When the sample liquid reaches the fill level, the sample valve 88 is closed. Measurement of an equilibrium time period of about 4.5 minutes is then started. At the expiration of the equilibrium time period, the pressure in the measuring cell 66 is recorded and stored as the sample pressure measurement. Using the sample pressure measurement, the zero pressure measurement and the site elevation, the RVP microprocessor 56 calculates the Reid vapor pressure of the sample liquid. This Reid vapor pressure measurement is displayed on the LCD display of the operator interface 58 and is stored in memory.

Figure 4:
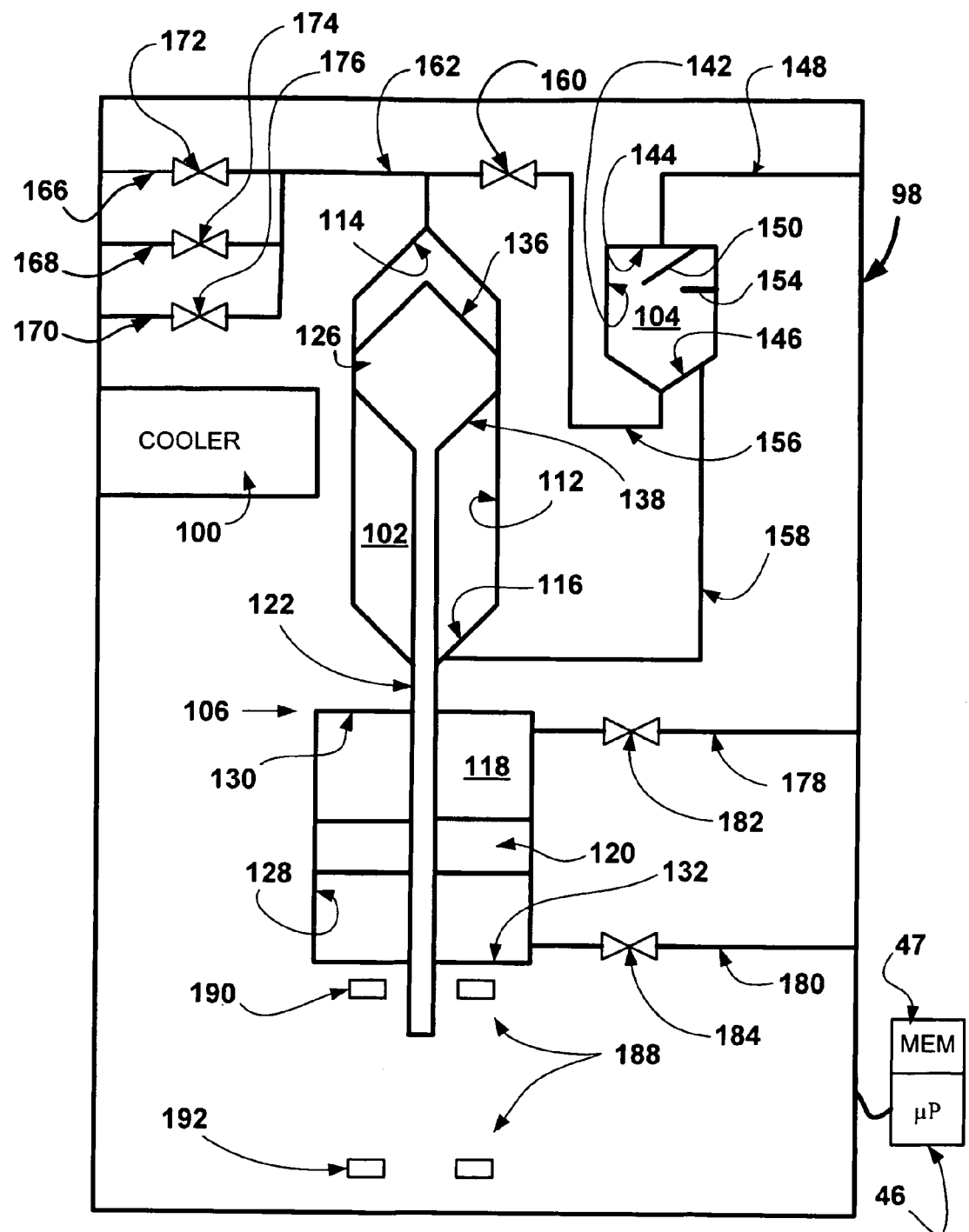
FIG. 4 is a schematic view of a first embodiment of an air saturation unit of the vapor pressure analyzer.

Referring now to FIG. 4, the air saturation process assembly 16 includes an air saturation unit 98 that generally comprises a cooler 100, a circulation chamber 102, an aeration chamber 104 and a pump assembly 106. The air saturation unit 98 is enclosed in an explosion-proof housing 108 having an enlarged opening that is closed by a pivotable door 110. The circulation chamber 102, the aeration chamber 104 and a pump chamber 118 of the pump assembly 106 may be formed in one or more metal structures. For example, the circulation chamber 102, the aeration chamber 104 and the pump chamber 118 may be formed in three interconnected metal structures.

The cooler 100 may be a thermoelectric cooler, which is a device that uses the Peltier effect to create a heat flux between the junction of two different types of materials. A typical thermoelectric cooler is a sandwich formed by two ceramic plates with an array of small Bismuth Telluride cubes ("couples") in between. When a DC current is applied, heat is moved from one side of the cooler to the other, where it is dissipated by a heatsink. The "cold" side of the cooler 100 is disposed inside the air saturation unit 98, whereas the heatsink of the cooler 100 is disposed outside the air saturation unit 98. The cooler 100 is connected to the AS microprocessor 46, which controls the cooler 100 to maintain the temperature inside the air saturation unit 98 at a temperature in a range from 32° F. to about 40° F., more specifically at a temperature of about 33° F.

The circulation chamber 102 is capable of holding 10 ml of sample liquid and is defined by a cylindrical side surface 112, a conical top surface 114 and a conical bottom surface 116.

The pump assembly 106 generally includes the piston chamber 118, a cylindrical piston 120, a shaft 122 and a plunger 126. The piston chamber 118 is located below the circulation chamber 102 and is defined by a cylindrical side surface 128, a top end surface 130 and a bottom end surface 132. The shaft 122 extends through the piston chamber 118 and into the circulation chamber 102. A top end of the shaft 122 is secured to a plunger 126 disposed in the circulation chamber 102. A lower portion of the shaft 122 extends through, and is fixedly secured to, the piston 120, which is movably disposed inside the piston chamber 118. A bottom end of the shaft 122 is disposed below the piston chamber 118. The plunger 126 has a conical upper surface 136 that conforms to the top surface 114 of the circulation chamber 102 and a conical lower surface 138 that conforms to the bottom surface 116 of the circulation chamber 102. The plunger 126 is movable between a top position, wherein the upper surface 136 adjoins the top surface 114 of the circulation chamber 102, and a bottom position, wherein the lower surface 138 adjoins the bottom surface 116 of the circulation chamber 102. The conformance of the plunger 126 with the top and bottom surfaces 118, 120 of the circulation chamber 102 (as described above) helps expel air from the circulation chamber 102 when the plunger 126 moves to the top or bottom position.

The aeration chamber 104 is defined by a cylindrical side surface 142, a top surface 144 and conical bottom surface 146. A vent opening is formed in the top surface 144 and is connected to a vent line 148. A splash guard 150 extends downwardly at an oblique angle from the top surface 144 and is positioned below the vent opening. The splash guard 150 is sized to cover (as viewed from the bottom surface 146) a substantial portion of the top surface 144 disposed around the vent opening. In this manner, the splash guard 150 prevents sample liquid from splashing out the vent opening when the sample liquid is circulated, as will be described more fully below. A level sensor 154 is disposed inside the aeration chamber 104 and is operable to determine when the level of sample liquid inside the aeration chamber 104 reaches a predetermined fill level. The level sensor 154 may be a thermistor that is heated by electrical current flowing therethrough. When the thermistor is contacted by sample liquid, the thermistor cools, thereby increasing the current flow therethrough, which provides an indication that the fill level has been reached. When filled to the fill level, the aeration chamber 104 holds about 2.5 ml of sample liquid.

The aeration chamber 104 is connected to the circulation chamber 102 by a first circulation line 156 and a second circulation line 158. The first circulation line 156 extends from an opening in the apex of the bottom surface 146 of the aeration chamber 104 to an opening in the apex of the top surface 114 of the circulation chamber 102. The second circulation line 158 extends from an opening in the bottom surface 146 of the aeration chamber 104 to an opening in the bottom surface 116 of the circulation chamber 102. A solenoid-actuated circulation valve 160 is connected into the first circulation line 156. An I/O line 162 is connected to the first circulation line 156, between the circulation valve 160 and the opening in the apex of the top surface 114 of the circulation chamber 102. The I/O line 162 is connected to a sample inlet line 166, a sample outlet line 168 and a drain line 170. A solenoid-actuated sample valve 172 is connected into the sample inlet line 166, a solenoid-actuated transfer valve 174 is connected into the sample outlet line 168 and a solenoid-actuated drain valve 176 is connected into the drain line 170. The sample inlet line 166 is connected to the sample inlet line 26 of the sample system 12, and the sample outlet line 168 is connected to the sample input line 72 of the RVP unit 64. The circulation valve 160, the sample valve 172, the transfer valve 174 and the drain valve 176 are all normally closed and are connected to, and controlled by, the AS microprocessor 46.

First and second air lines 178, 180 are connected to the piston chamber 118. The first air line 178 is connected to a top opening in the side surface 128, toward the top end surface 130, and the second air line 180 is connected to a bottom opening in the side surface 128, toward the bottom end surface 132. Solenoid-actuated, normally-closed, first and second air valves 182, 184 are connected into the first and second air lines 178, 180, respectively, and are connected to the AS microprocessor 46. The first and second air valves 182, 184 control the movement of the piston 120 and, thus, the movement of the shaft 122 and the plunger 126. The opening and closing of the first and second air valves 182, 184, in turn, are controlled by the AS microprocessor 46 using inputs from a position detection assembly 188 that determines when the plunger 126 is in the top position and the bottom position. When the first air valve 182 is opened and the second air valve is closed, pressurized air enters the piston chamber 118 through the first air line 178 and forces the piston 120 downward, which causes the shaft 122 and the plunger 126 to move downward. When the plunger 126 reaches the bottom position, as determined by the position detection assembly 188, the first air valve 182 closes. When the first air valve 182 is closed and the second air valve 184 is opened, pressurized air enters the piston chamber 118 through the second air line 180 and forces the piston 120 upward, which causes the shaft 122 and the plunger 126 to move upward. When the plunger 126 reaches the top position, as determined by the position detection assembly 188, the second air valve 184 closes. When the plunger 126 moves upward or downward, as the case may be, air in the piston chamber 118 in the direction of movement of the plunger 126 is compressed and is permitted to escape the piston chamber 118 through a vent (not shown).

The position detection assembly 188 includes first and second sensors 190, 192 connected to the AS microprocessor 46. The first and second sensors 190, 192 may be photo interrupt sensors or magnetic proximity sensors. The first sensor 190 is disposed proximate to the piston cavity 118 and closely adjacent to a travel path of the shaft 122. The second sensor 192 is disposed distal to the piston cavity 118 and is also positioned closely adjacent to the travel path of the shaft 122. The first and second sensors 190, 192 are positioned such that the shaft 122 is not detected by either the first sensor 190 or the second sensor 192 when the plunger 126 is in the top position and is detected by both the first sensor 190 and the second sensor 192 only when the plunger 126 is in the bottom position. Thus, if neither the first sensor 190 nor the second sensor 192 detects the shaft 122, the plunger 126 is determined to be in the top position, whereas if both the first and second sensors 190, 192 detect the shaft 122, the plunger 126 is determined to be in the bottom position. If the first sensor 190, but not the second sensor 192 detects the shaft 122, the plunger 126 is determined to be intermediate between the top and bottom positions.

Figure 5:
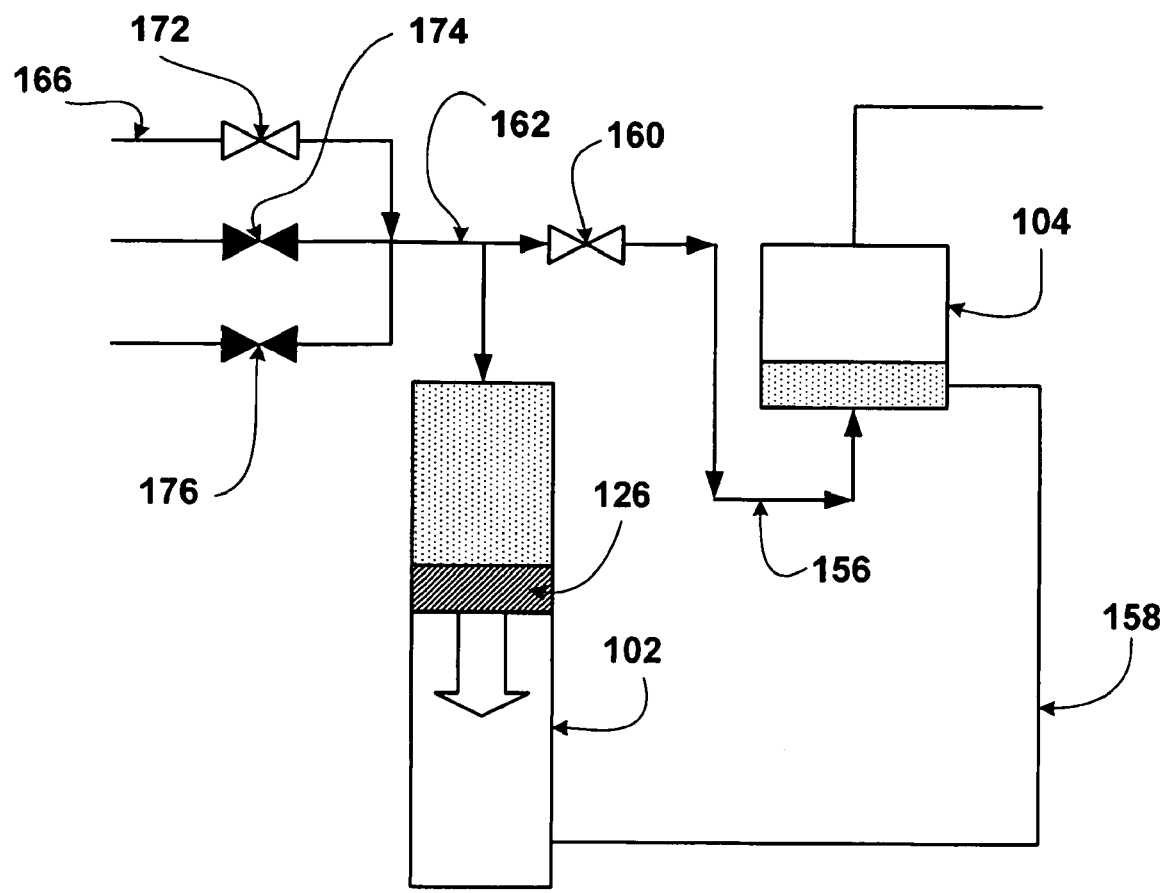
FIG. 5 is a functional schematic view of a portion of the first embodiment of the air saturation unit during a first stage of operation.
Figure 6:
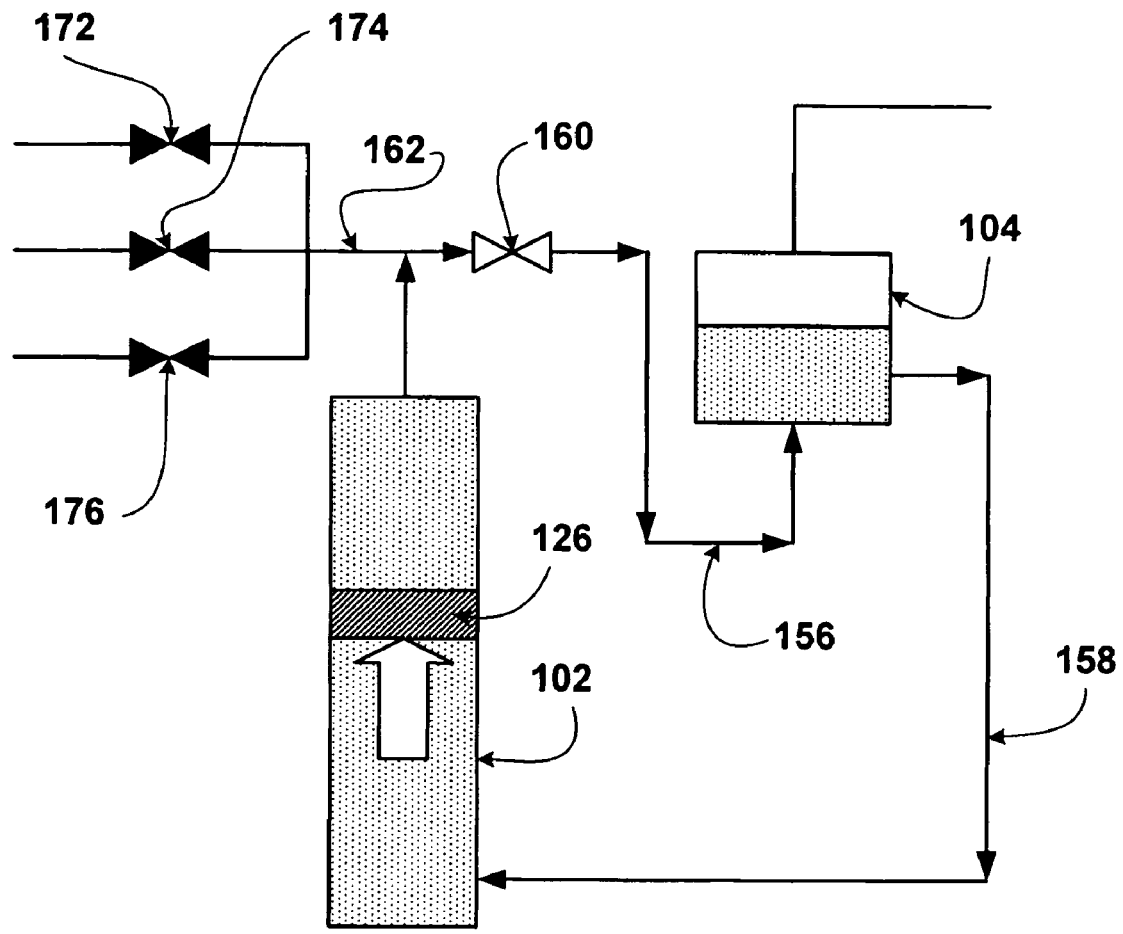
FIG. 6 is a functional schematic view of a portion of the first embodiment of the air saturation unit during a second stage of operation.
Figure 7:
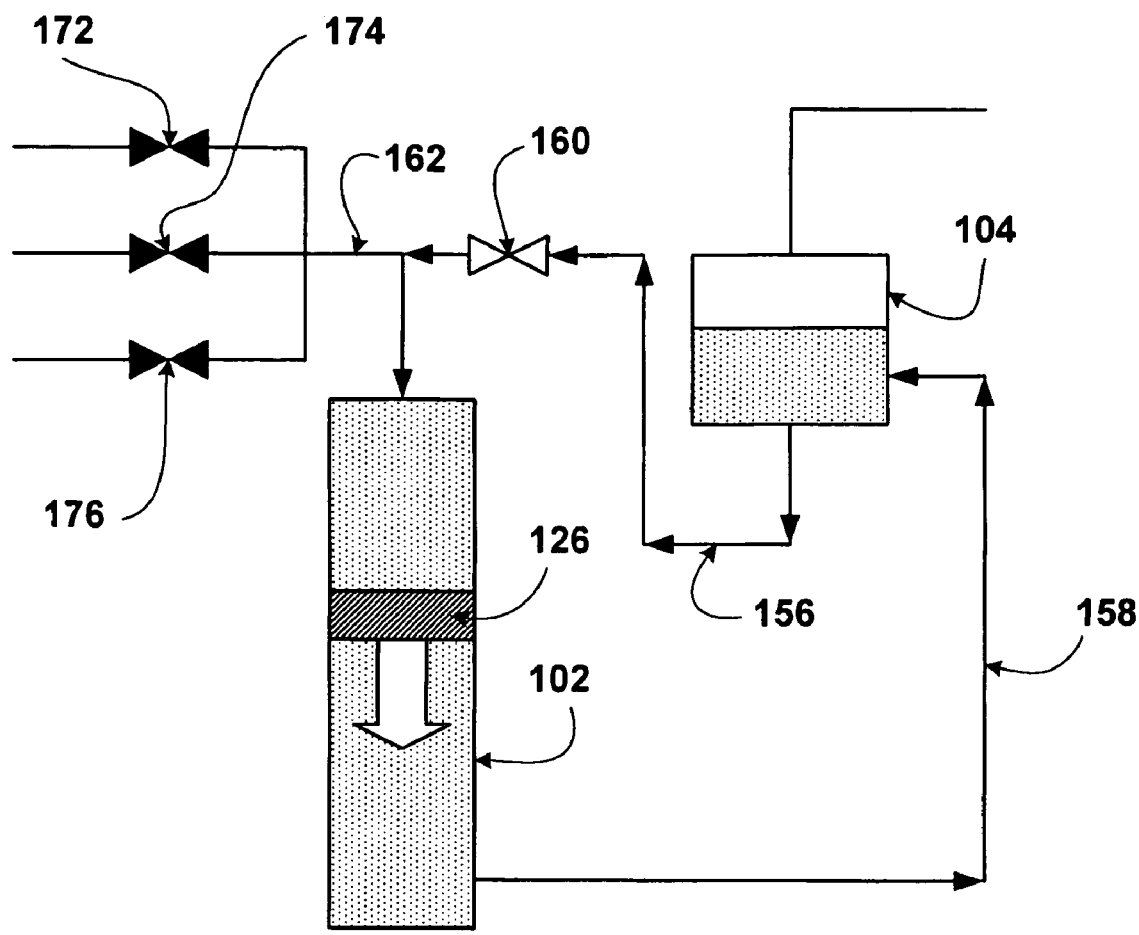
FIG. 7 is a functional schematic view of a portion of the first embodiment of the air saturation unit during a third stage of operation.

The AS microprocessor 46 controls the opening and closing of the circulation valve 160, the sample valve 172, the transfer valve 174, the drain valve 176 and the first and second air valves 182, 184 pursuant to an aeration software routine stored in memory 47 and executed by the AS microprocessor 46. When executed by the AS microprocessor 46, the aeration software routine performs an aeration method, which will now be described with reference to FIGS. 5-11. It should be noted that in FIGS. 5-11, the piston chamber 118 and the piston 120 are not shown. Initially, the plunger 126 is in the top position and the sample valve 172, the transfer valve 174, the drain valve 176 and the first and second air valves 182, 184 are closed. In a first stage of the aeration method, the sample valve 172 and the circulation valve 160 are opened. Sample liquid flows through the sample inlet line 166, the I/O line 162 and the first circulation line 156 and enters both the circulation chamber 102 and the aeration chamber 104 and causes the plunger 126 to move downward, as shown in FIG. 5. When the sample liquid in the aeration chamber 104 reaches the fill level, the circulation valve 160 closes, and when the plunger 126 reaches the bottom position, the sample valve 172 closes. At this point, the circulation chamber 102 above the plunger 126 is filled with sample liquid and the aeration chamber 104 contains the sample liquid up to the fill level. In a second stage, the circulation valve 160 and the second air valve 184 are opened. Air enters the piston chamber 118 below the piston 120 and moves the piston 120 and, thus, the plunger 126 upward. The upward movement of the plunger 126 causes sample liquid to be expelled from the circulation chamber 102 and to pass through the first circulation line 156 into the aeration chamber 104. At the same time, sample liquid is drawn out of the aeration chamber 104 through the second circulation line 158 and into the circulation chamber 102, below the plunger 126, as shown in FIG. 6. When the plunger 126 reaches the top position, the second air valve 184 closes. At this point, the circulation chamber 102 below the plunger 126 is filled with sample liquid and the aeration chamber 104 contains the sample liquid up to the fill level. In a third stage, the first air valve 182 opens and air enters the piston chamber 118 above the piston 120 and moves the piston 120 and, thus, the plunger 126 downward. The downward movement of the plunger 126 causes sample liquid to be expelled from the circulation chamber 102 and to pass through the second circulation line 158 into the aeration chamber 104. At the same time, sample liquid is drawn out of the aeration chamber 104 through the first circulation line 156 and into the circulation chamber 102, above the plunger 126, as shown in FIG. 7. When the plunger 126 reaches the bottom position, the first air valve 182 is closed. At this point, the circulation chamber 102 above the plunger 126 is filled with sample liquid and the aeration chamber 104 contains the sample liquid up to the fill level. Stages two and three are then repeated a predetermined number of times, such as eight, ten, twelve, etc. times. In this manner, sample liquid is moved back and forth (circulated) between the circulation chamber 102 and the aeration chamber 104 a predetermined number of times. This back and forth movement of the sample liquid saturates the sample liquid with air.

Figure 8:
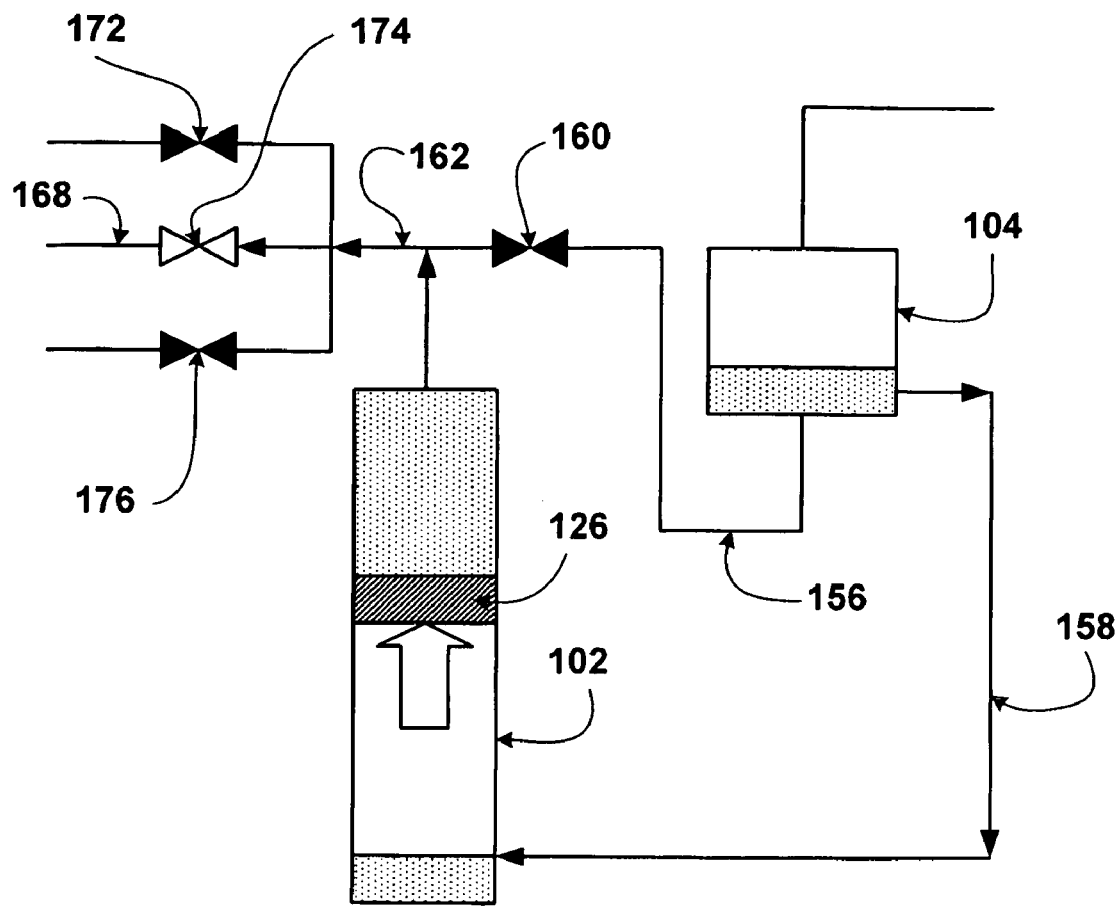
FIG. 8 is a functional schematic view of a portion of the first embodiment of the air saturation unit during a fourth stage of operation.

When the repetition of stages two and three is completed, the plunger 126 is in the bottom position, the circulation chamber 102 above the plunger 126 is filled with the sample liquid and the aeration chamber 104 contains the sample liquid up to the fill level. At this point, the temperature of the sample liquid in the circulation chamber 102 is in a range of from about 32° F. to about 40° F., more specifically about 33° F. A fourth stage is entered when the AS microprocessor 46 receives the fill request signal from the RVP microprocessor 56 to provide sample liquid to the RVP unit 64. In the fourth stage, the circulation valve 160 is closed, the transfer valve 174 is opened and the second air valve 184 is opened. Air enters the piston chamber 118 below the piston 120 and moves the piston 120 and, thus, the plunger 126 upward. The upward movement of the plunger 126 causes sample liquid to be expelled from the circulation chamber 102 and to pass through the I/O line 162 and the sample outlet line 168, as shown in FIG. 8. From the sample outlet line 168, the sample liquid travels to the sample input line 72 of the RVP unit 64. The upward movement of the plunger 126, however, is not continuous in the fourth stage due to the sample valve 172 in the RVP unit 64 closing between the false fills and the measured fill of the measuring cell 66. The upward movement of the plunger 126 during the fourth stage also causes sample liquid to be drawn out of the aeration chamber 104 through the second circulation line 158 and into the circulation chamber 102, below the plunger 126.

Figure 9:
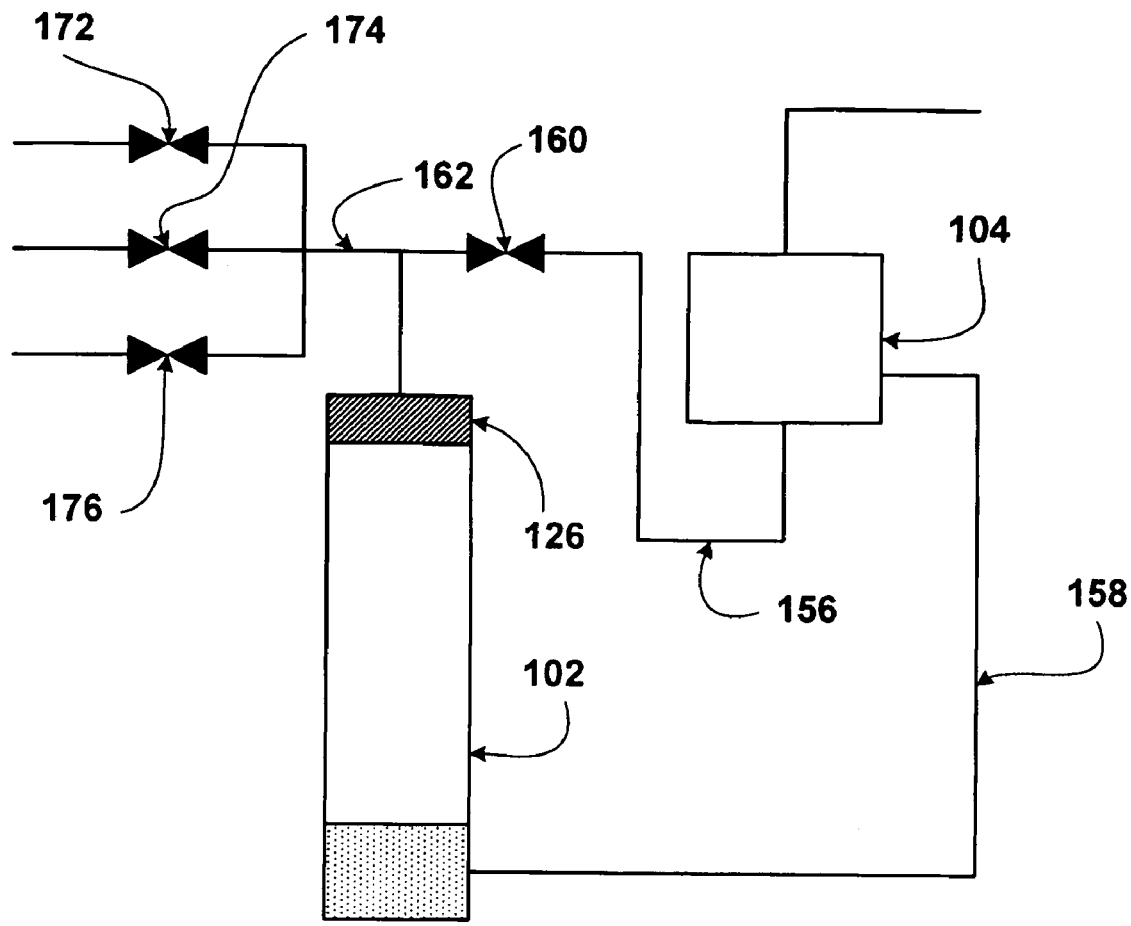
FIG. 9 is a functional schematic view of a portion of the first embodiment of the air saturation unit at the end of the fourth stage of operation.
Figure 10:
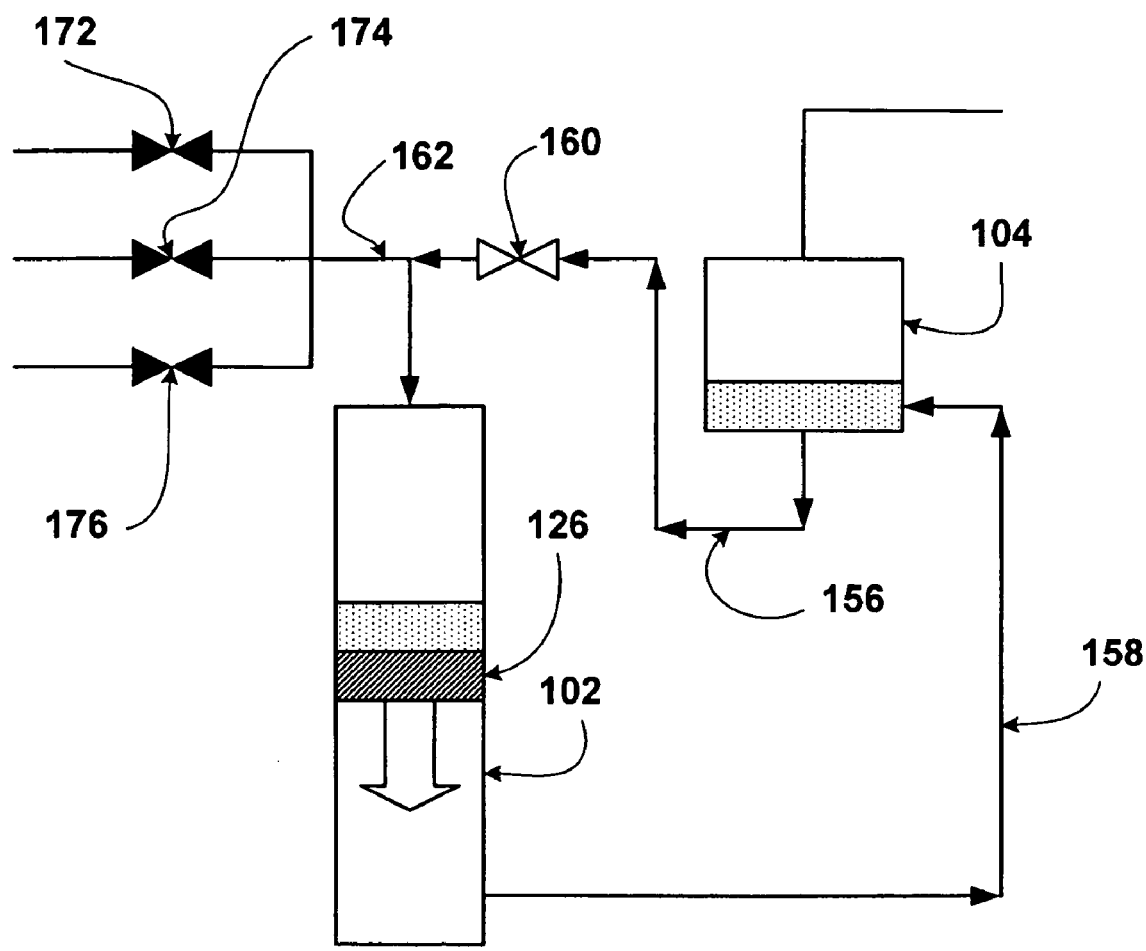
FIG. 10 is a functional schematic view of a portion of the first embodiment of the air saturation unit during a fifth stage of operation.
Figure 11:
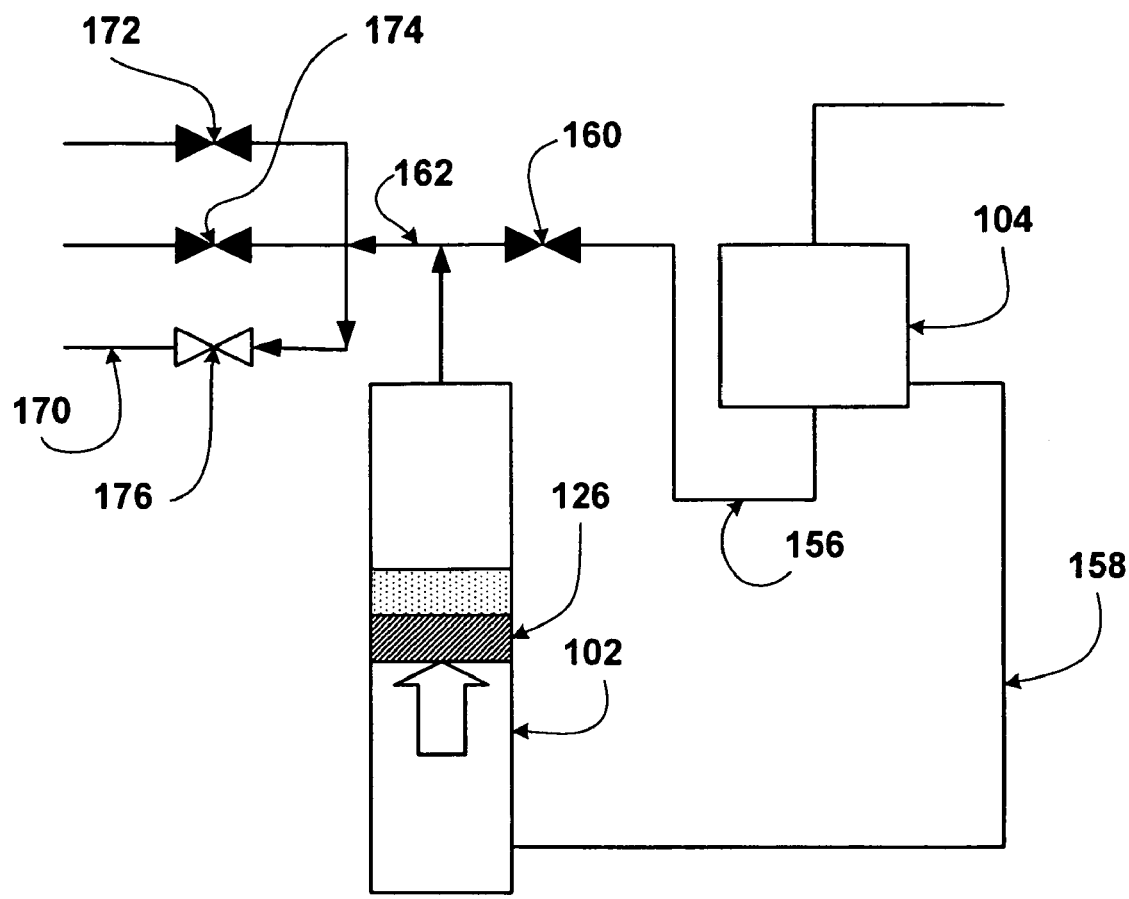
FIG. 11 is a functional schematic view of a portion of the first embodiment of the air saturation unit during a sixth stage of operation.

After the measuring cell 66 of the RVP unit 64 is provided with the measured fill of the sample liquid, the transfer valve 174 and the second air valve 184 are both closed. At this point, the remaining sample liquid from the aeration chamber 104 is now located in the circulation chamber 102, below the piston 120, as shown in FIG. 9. Fifth and sixth stages of the aeration method are then performed to move the remaining sample liquid to the drain. In the fifth stage, the circulation valve 160 and the first air valve 182 are opened. Air enters the piston chamber 118 above the piston 120 and moves the piston 120 and, thus, the plunger 126 downward. The downward movement of the plunger 126 causes sample liquid to be expelled from the bottom of the circulation chamber 102, pass through the second circulation line 158 and the aeration chamber 104 and reenter the top of the aeration chamber 104, as shown in FIG. 10. When the plunger 126 reaches the bottom position, the first air valve 182 and the circulation valve 160 are closed. At this point, the circulation chamber 102 above the plunger 126 contains the remaining sample liquid and the aeration chamber 104 is empty. In the sixth stage, the drain valve 176 is opened and the second air valve 184 is opened. Air enters the piston chamber 118 below the piston 120 and moves the piston 120 and, thus, the plunger 126 upward. The upward movement of the plunger 126 causes the remaining sample liquid to be expelled from the circulation chamber 102 and to pass through the I/O line 162 to the drain line 170 and thence to the drain, as shown in FIG. 11.

Figure 12:
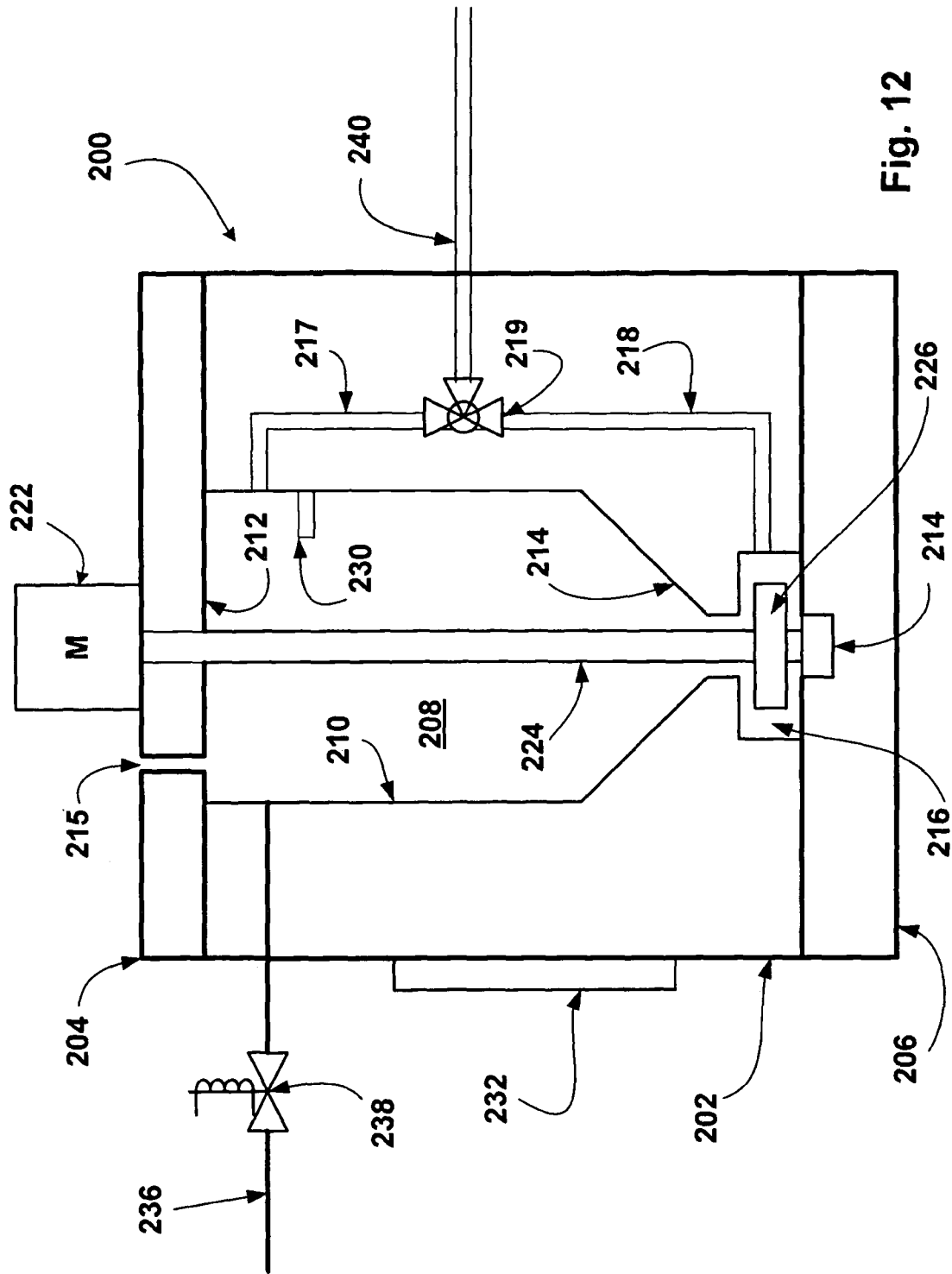
FIG. 12 is a schematic view of a second embodiment of an air saturation unit of the vapor pressure analyzer.

Referring now to FIG. 12, there is shown a second air saturation unit 200 embodied in accordance with a second embodiment of the invention. The second air saturation unit 200 may be used in the air saturation process assembly 16 in lieu of the air saturation unit 98. The second air saturation unit 200 includes a main structure 202 secured between top and bottom structures 204, 206. The main structure 202 and the top and bottom structures 204, 206 may be a comprised of metal, such as stainless steel. The second air saturation unit 200 has a saturation chamber 208 defined by a cylindrical interior side surface 210 of the main structure 202, an interior surface 212 of the top structure 204 and a conical interior bottom surface 214 of the main structure 202. A vent passage 215 for the saturation chamber 208 extends through the top structure 204. A pump chamber 216 is disposed below the saturation chamber 208 and is connected thereto by a short lower passage that extends through an opening in the bottom surface 214 at the apex thereof. Upper and lower circulation passages 217, 218 extending through the main structure 202 connect the pump chamber 216 to an upper portion of the saturation chamber 208. The upper circulation passage 217 communicates with the saturation chamber 208 through an opening in an upper portion of the side surface 210. A solenoid-actuated, three-way transfer valve 219 is connected between the upper and lower circulation passages 217, 218. Below the pump chamber 210, a bearing 214 is held securely in a cavity formed in the bottom structure 206. A top passage 220 extends through the top structure 204. A brushless electric motor 222 is mounted to the top structure 204 and is operable to rotate a shaft 224, which extends through the top passage 220 and the saturation chamber 208 and is secured to a cylindrical impeller 226 disposed in the pump chamber 228. A bottom end of the shaft 224 is rotatably disposed in the bearing 214. The operation of the electric motor is controlled by the AS microprocessor 46.

A level sensor 230 is disposed inside the saturation chamber 208 and is operable to determine when the level of sample liquid inside the saturation chamber 208 reaches a predetermined fill level. The level sensor 230 is connected to the AS microprocessor 46 and may be a thermistor that is heated by electrical current flowing therethrough. When the thermistor is contacted by sample liquid, the thermistor cools, thereby increasing the current flow therethrough, which provides an indication that the fill level has been reached.

A cooler 232 is mounted to the main structure 202 and is connected to the AS microprocessor 46, which controls the cooler 232 to maintain the temperature inside the saturation chamber 208 at a temperature in a range from about 32° F. to about 40° F., more specifically at a temperature of about 33° F. The cooler 232 may be a thermoelectric cooler.

A sample inlet line 236 connects the sample input line 26 of the sample system 12 to the saturation chamber 208. A solenoid-actuated, normally closed sample valve 238 is connected into the sample inlet line 236. A sample outlet line 240 connects the transfer valve 219 to the sample input line 72 of the RVP unit 64. Both the sample valve 238 and the transfer valve 219 are connected to the AS microprocessor 46.

The AS microprocessor 46 controls the opening and closing of the sample valve 238 and the operation of the electric motor 222 and the transfer valve 219 pursuant to a second aeration software routine stored in memory 47 and executed by the AS microprocessor 46. When executed by the AS microprocessor 46, the second aeration software routine performs an aeration method, which begins with the opening of the sample valve 238. Sample liquid from the sample system 12 travels through the sample inlet line 236 and into the saturation chamber 208. When the sample liquid in the saturation chamber 208 reaches the fill level, as determined by the level sensor 230, the sample valve 238 closes. The transfer valve 219 is then controlled to make a flow connection between the upper and lower circulation passages 217, 218, while blocking fluid flow to the sample outlet line 240. The electric motor 22 is provided with power so as to rotate the shaft 224 and, thus, the impeller 226, thereby causing sample liquid in the saturation chamber 208 to be drawn into the pump chamber 216 and moved through the lower circulation passage 218 and thence through the upper circulation passage 217 to the top of the saturation chamber 208. In this manner, sample liquid is circulated from the bottom of the saturation chamber 208 to the top of the saturation chamber 208, thereby saturating the sample liquid with air. After a predetermined period of time, the transfer valve 219 is controlled to block the flow connection between the upper and lower circulation passages 217, 218 and, instead to make a flow connection between the lower circulation passage 218 and the sample outlet line 240. As a result, the sample liquid from the bottom of the saturation chamber 208 is moved through the lower circulation passage 217 to the sample outlet line 240. From the sample outlet line 240, the sample liquid travels to the sample input line 72 of the RVP unit 64. The air-saturated sample liquid has a temperature in a range from about 32° F. to about 40° F., more specifically about 33° F.

While the invention has been shown and described with respect to particular embodiments thereof, those embodiments are for the purpose of illustration rather than limitation, and other variations and modifications of the specific embodiments herein described will be apparent to those skilled in the art, all within the intended spirit and scope of the invention. Accordingly, the invention is not to be limited in scope and effect to the specific embodiments herein described, nor in any other way that is inconsistent with the extent to which the progress in the art has been advanced by the invention.

What is claimed is:

1. An analyzer for measuring the vapor pressure of a hydrocarbon liquid, the analyzer comprising:
    a pressure measuring system comprising:
        a measuring cell for holding the hydrocarbon liquid; and
        a pressure sensor for measuring the pressure within the measuring cell; and
    an air saturation system connected to the pressure measuring system and operable to provide the hydrocarbon liquid to the measuring cell, the air saturation system comprising:
        first and second chambers, each having first and second openings;
        a pump operable to move the hydrocarbon liquid back and forth between the first and second chambers so as to saturate the hydrocarbon liquid with air, the pump comprising a plunger disposed in the first chamber and being movable between first and second positions within the first chamber, the plunger being disposed between the first and second openings of the first chamber;
a first circulation line with a circulation valve connected therein, the first circulation line connecting the first opening of the first chamber to the first opening of the second chamber;
a second circulation line connecting the second opening of the first chamber to the second opening of the second chamber;
an inlet line with an inlet valve connected therein, the inlet line being connected to a source of the hydrocarbon liquid;
an outlet line with an outlet valve connected therein, the outlet line being connected to the pressure measuring system; and
an input/output line connecting the inlet line, the outlet line and the circulation line to the first opening of the first chamber.

2. The analyzer of claim 1, wherein the pressure measuring system further comprises a heater for heating the hydrocarbon liquid in the pressure measuring system.

3. The analyzer of claim 2, wherein the heater is controlled to heat the hydrocarbon liquid to a temperature of about 100° F.

4. The analyzer of claim 1, wherein the air saturation system further comprises a cooler for cooling the hydrocarbon liquid in the air saturation system.

5. The analyzer of claim 3, wherein the cooler comprises a thermoelectric cooler.

6. The analyzer of claim 5, wherein the cooler is controlled to cool the hydrocarbon liquid to a temperature in a range from about 32° F. to about 40° F.

7. The analyzer of claim 1, wherein the air saturation system further comprises:
a microprocessor connected to the pump, the at least one air valve, the circulation valve, the inlet valve and the outlet valve to control their operation; and
computer readable medium having computer-readable instructions stored thereon for execution by the microprocessor to perform an aeration method comprising:
(a.) opening the inlet valve and the circulation valve to permit the hydrocarbon liquid to flow into the second chamber and into the first chamber on a first side of the plunger;
(b.) when the hydrocarbon liquid reaches a predetermined fill level in the second chamber, closing the circulation valve;
(c.) when the plunger reaches the second position, closing the inlet valve;
(d.) opening the circulation valve;
(e.) moving the plunger to the first position, thereby causing hydrocarbon liquid from the first chamber to flow out the first opening in the first chamber and travel through the first circulation line to the second chamber and hydrocarbon liquid from the second chamber to flow out the second opening in the second chamber and travel through the second circulation line to the first chamber on a second side of the plunger;
(f.) when the plunger reaches the first position, moving the plunger back to the second position, thereby causing hydrocarbon liquid from the first chamber to flow out the second opening in the first chamber and travel through the second circulation line to the second chamber and hydrocarbon liquid from the second chamber to flow out the first opening in the second chamber and travel through the first circulation line to the first chamber on the first side of the plunger;
(g.) repeating steps (e.) and (f.) a predetermined number of times; and
(h.) closing the circulation valve, opening the outlet valve and moving the plunger to the first position, thereby causing hydrocarbon liquid from the first chamber to flow out the first opening in the first chamber and travel through the input/output line and thence the outlet line to the pressure measuring system.

8. The analyzer of claim 7, wherein the pump further comprises:
a piston chamber;
a piston disposed in the piston chamber and movable between first and second positions within the piston chamber;
a shaft secured to the piston; and
wherein the plunger is secured to the shaft and is movable in response to movement of the piston such that when the piston is in the first position, the plunger is in the first position, and when the piston is in the second position, the plunger is in the second position.

9. The analyzer of claim 8, wherein the piston chamber has a first opening on a first side of the piston and a second opening on a second side of the piston; and
wherein the pump further comprises at least one air valve connected to the first and second openings in the piston chamber to selectively control a supply of pressurized air to the first and second openings, whereby when pressurized air is only provided to the second opening, the pressurized air moves the piston to the first position and when pressurized air is only provided to the first opening, the pressurized air moves the piston to the second position; and
wherein in the aeration method, the plunger is moved to the first position by controlling the at least one air valve to only provide pressurized air to the second opening of the piston chamber and the plunger is moved to the second position by controlling the at least one air valve to only provide pressurized air to the first opening of the piston chamber.

10. An analyzer for measuring the vapor pressure of a hydrocarbon liquid, the analyzer comprising:
a pressure measuring system comprising:
a measuring cell for holding the hydrocarbon liquid; and
a pressure sensor for measuring the pressure within the measuring cell; and
an air saturation system connected to the pressure measuring system and operable to provide the hydrocarbon liquid to the measuring cell, the air saturation system comprising:
a circulation chamber with opposing first and second ends, the circulation chamber having a first opening disposed toward the first end and a second opening disposed toward the second end;
a plumbing system that connects the first and second openings together;
a pump operable to move hydrocarbon liquid so as to saturate the hydrocarbon liquid with air, the pump comprising a plunger disposed in the circulation chamber and being movable between first and second positions, the plunger being disposed between the first and second openings of the circulation chamber; and
wherein the plumbing system comprises
an aeration chamber having first and second openings;
a first circulation line connecting the first opening of the aeration chamber to the first opening of the circulation chamber;

a second circulation line connecting the second opening of the aeration chamber to the second opening of the circulation chamber; and a circulation valve connected into the first circulation line.

11. The analyzer of claim 10, wherein the air saturation system further comprises a cooler operable to cool the hydrocarbon liquid in the air saturation system to a temperature in a range from about 32° F. to about 40° F.

12. The analyzer of claim 10, wherein the pressure measuring system further comprises a heater operable to heat the hydrocarbon liquid in the pressure measuring system to a temperature of about 100° F.

13. The analyzer of claim 12, wherein the pump further comprises:

a piston chamber having first and second openings;

a piston disposed in the piston chamber and movable between first and second positions, the piston being positioned such that the first opening of the piston chamber is disposed on a first side of the piston and the second opening of the piston chamber is disposed on the second side of the piston;

a shaft secured to the piston and having a first the plunger; and at least one air valve connected to the first and second openings in the piston chamber to selectively control a supply of pressurized air to the first and second openings, whereby when pressurized air is only provided to the second opening, the pressurized air moves the piston to the first position and when pressurized air is only provided to the first opening, the pressurized air moves the piston to the second position; and wherein the plunger is movable in response to movement of the piston such that when the piston is in the first position, the plunger is in the first position, and when the piston is in the second position, the plunger is in the second position.

14. An analyzer for measuring the vapor pressure of a hydrocarbon liquid, the analyzer comprising:

a pressure measuring system comprising:

a measuring cell for holding the hydrocarbon liquid; and a pressure sensor for measuring the pressure within the measuring cell; and an air saturation system connected to the pressure measuring system and operable to provide the hydrocarbon liquid to the measuring cell, the air saturation system comprising:

a circulation chamber with opposing first and second ends, the circulation chamber having a first opening disposed toward the first end and a second opening disposed toward the second end;

a plumbing system that connects the first and second openings together;

a pump operable to move hydrocarbon liquid through the plumbing system from the first opening to the second opening so as to saturate the hydrocarbon liquid with air, wherein the pump comprises:

a pump chamber disposed below the circulation chamber, the pump chamber being connected to the first opening of the circulation chamber;

an impeller disposed in the pump chamber;

a shaft having an end connected to the impeller; and an electric motor operable to rotate the shaft and, thus, the impeller.

15. The analyzer of claim 14, wherein the plumbing system comprises a first circulation line connected to the pump chamber; and a second circulation line connected to the circulation chamber;

a circulation valve connecting the first and second circulation lines.

16. The analyzer of claim 15, wherein the plumbing system further comprises:

an outlet line with an outlet valve connected therein, the outlet line being connected to the pressure measuring system; and wherein the circulation valve is a three-way valve having a first port connected to the first circulation line, a second port connected to the second circulation line and a third port connected to the outlet line, and wherein the valve is movable between first and second connection states, wherein when the circulation valve is in the first connection state, the circulation valve permits the hydrocarbon liquid to flow from the first circulation line to the second circulation line and blocks the flow of hydrocarbon liquid to the outlet line, and wherein when the circulation valve is in the second connection state, the circulation valve permits the hydrocarbon liquid to flow from the first circulation line to the outlet line and blocks the flow of hydrocarbon liquid to the second circulation line;

wherein when the circulation valve is in the first connection state and the motor is provided with power to rotate the impeller, the hydrocarbon liquid in the circulation chamber is drawn through the first opening into the pump chamber and then is moved through the first and second circulation lines and enters the circulation chamber through the second opening therein; and wherein when the circulation valve is in the second connection state and the motor is provided with power to rotate the impeller, the hydrocarbon liquid in the circulation chamber is drawn through the first opening into the pump chamber and then is moved through the first circulation and thence the outlet line to the pressure measuring system.

17. The analyzer of claim 10, wherein the aeration chamber comprises a top surface with a vent opening and a splash guard disposed below the vent opening.

18. The analyzer of claim 10, wherein the pump further comprises a fluid-actuated piston connected to the plunger, the fluid-actuated piston being operable to move the plunger between the first and second positions.

19. The analyzer of claim 18, wherein the plumbing system further comprises:

an inlet line connecting the circulation chamber and the first circulation line to a source of the hydrocarbon liquid; and an inlet valve connected into the inlet line.

20. The analyzer of claim 19, further comprising a controller connected to the circulation valve, the fluid-actuated piston and the inlet valve and operable to perform an aeration method comprising:

(a.) opening the inlet valve and the circulation valve to permit the hydrocarbon liquid to flow into the aeration chamber and into the circulation chamber on a first side of the plunger;

(b.) when the hydrocarbon liquid reaches a predetermined fill level in the aeration chamber, closing the circulation valve;

(c.) when the plunger reaches the second position, closing the inlet valve;

(d.) opening the circulation valve;

(e.) moving the plunger to the first position, thereby causing hydrocarbon liquid from the circulation chamber to flow out the first opening in the circulation chamber and travel through the first circulation line to the aeration chamber and hydrocarbon liquid from the aeration chamber to flow out the second opening in the aeration chamber and travel through the second circulation line to the circulation chamber on a second side of the plunger; and (f.) when the plunger reaches the first position, moving the plunger back to the second position, thereby causing hydrocarbon liquid from the circulation chamber to flow out the second opening in the circulation chamber and travel through the second circulation line to the aeration chamber and hydrocarbon liquid from the aeration chamber to flow out the first opening in the aeration chamber and travel through the first circulation line to the circulation chamber on the first side of the plunger.

* * * * *